United States Patent [19]

McEvoy et al.

[11] 4,435,329
[45] Mar. 6, 1984

[54] SUBSTITUTED N-(ω-AROYLPROPIONYL) DERIVATIVES OF α-AMINO ACIDS AND ESTERS THEREOF

[75] Inventors: Francis J. McEvoy, Pearl River; Jay D. Albright, Nanuet, both of N.Y.

[73] Assignee: American Cyanamid Company, Stamford, Conn.

[21] Appl. No.: 312,119

[22] Filed: Oct. 16, 1981

[51] Int. Cl.³ ............... C07C 149/40; C07C 149/43; C07C 153/023
[52] U.S. Cl. .................................. 260/455 R; 560/10; 560/16; 548/469
[58] Field of Search ............... 260/455 R; 560/10, 16

[56] References Cited

U.S. PATENT DOCUMENTS 4,154,960 5/1979 Ondetti et al. ............... 260/455 R

Primary Examiner—Henry R. Jiles
Assistant Examiner—Robert C. Whittenbaugh
Attorney, Agent, or Firm—Mary-Ellen M. Timbers

[57] ABSTRACT

Novel compounds are described having the formula $$\underset{\text{ARYL-C-Z-C-N-CHCO}_2\text{R}_3}{\overset{\text{O}\quad\text{O}\quad\text{R}_1\;\text{R}_2}{\|\quad\;\|\quad\;|\quad\;|}}$$

wherein Z is

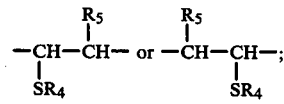

$R_1$ is hydrogen or a $C_1$–$C_4$ lower alkyl; $R_2$ is hydrogen, a $C_1$–$C_4$ lower alkyl, hydroxy-$R_8$-, lower alkyl-$R_8$-, mercapto-$R_8$-, cyclohexyl, cyclopentyl, phenyl, phenyl-$R_8$-, indolyl-$R_8$-, carboxy-$R_8$-, amino-$R_8$- or carbamoyl-$R_8$-, wherein $R_8$- is a divalent $C_1$–$C_6$ straight chain parafinic moiety; $R_3$ is hydrogen or $C_1$–$C_4$ lower alkyl; $R_4$ is hydrogen, lower alkanoyl, benzoyl or phenyl-substituted-lower alkanoyl; $R_5$ is hydrogen or a $C_1$–$C_4$ lower alkyl; $R_1$, $R_2$ and $R_5$ excluding tertiary butyl; ARYL is 1-naphthyl, 2-naphthyl, 4-chloro-1-naphthyl, 4-methoxy-1-naphthyl, 5,6,7,8-tetrahydro-1-naphthyl, 5,6,7,8-tetrahydro-2-naphthyl, 4-biphenylyl, 5-indanyl, 4-indanyl, phenyl, or substituted phenyl moieties having the formula

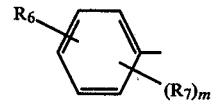

wherein $R_6$ is fluoro, chloro, bromo, trifluoromethyl, cyano, phenoxy, halophenoxy, phenylthio, halophenylthio, a $C_1$–$C_4$ lower alkyl or a $C_1$–$C_4$ lower alkoxy, and $R_7$ is chloro, fluoro, bromo, a $C_1$–$C_4$ lower alkyl or a $C_1$–$C_4$ lower alkoxy; and where m is an integer of zero, one or two; including individual optically active isomers; racemic mixtures thereof; non-toxic pharmacologically-acceptable salts of the foregoing; and mixtures of the foregoing. Processes of preparing such compounds are also described. Such compounds are useful in ameliorating hypertension in mammals.

21 Claims, No Drawings

SUBSTITUTED N-(ω-AROYLPROPIONYL) DERIVATIVES OF α-AMINO ACIDS AND ESTERS THEREOF

BRIEF SUMMARY OF THE INVENTION

1. Field Of The Invention

This invention relates to novel organic compounds which are substituted N-(ω-aroylpropionyl) derivatives of α-amino acids and esters thereof, and to processes of the therapeutic use of such compounds in the treatment of hypertension in mammals.

The applicants are not aware of any prior art patents or publications which, in their respective judgement, should be deemed to anticipate the compounds and processes described and claimed herein. By way of background, U.S. Pat. Nos. 4,226,775 and 4,192,878 are cited.

2. Description

The novel compounds of this invention include those of the class represented by the formula (11)

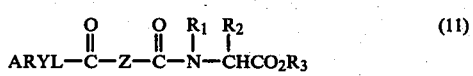

wherein Z is a divalent moiety selected from the class consisting essentially of

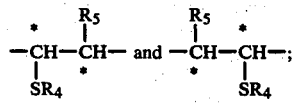

$R_1$ is selected from the class consisting essentially of hydrogen and lower alkyl having from 1 to 4 carbon atoms but excluding tertiary butyl; $R_2$ is selected from the class consisting essentially of hydrogen, lower alkyl having from 1 to 4 carbon atoms but excluding tertiary butyl; hydroxy-$R_8$-, lower alkyl-$R_8$-, mercapto-$R_8$-, cyclohexyl, cyclopentyl, phenyl, phenyl-$R_8$-, indolyl-$R_8$-, carboxy-$R_8$-, amino-$R_8$- and carbamoyl-$R_8$-, wherein $R_8$- is a divalent straight chain parafinic moiety having 1 to 6 carbon atoms; $R_3$ is selected from the class consisting essentially of hydrogen and lower alkyl having from 1 to 4 carbon atoms; $R_4$ is selected from the class consisting essentially of hydrogen, lower alkanoyl, benzoyl and phenyl-substituted-lower alkanoyl; $R_5$ is selected from the class consisting essentially of hydrogen and a lower alkyl having from 1 to 4 carbon atoms but excluding tertiary butyl; ARYL is selected from the class consisting essentially of 1-naphthyl, 2-naphthyl, 4-chloro-1-naphthyl, 4-methoxy-1-naphthyl, 5,6,7,8-tetrahydro-1-naphthyl, 5,6,7,8-tetrahydro-2-naphthyl, 4-biphenylyl, 5-indanyl, 4-indanyl, phenyl, and substituted phenyl moieties having the formula

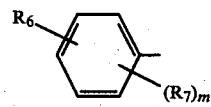

wherein $R_6$ is selected from the class consisting essentially of fluoro, chloro, bromo, trifluoromethyl, cyano, phenoxy, halophenoxy, phenylthio, halophenylthio, lower alkyl having from 1 to 4 carbon atoms, and lower alkoxy having from 1 to 4 carbon atoms, and $R_7$ is selected from the group consisting of chloro, fluoro, bromo, lower alkyl having from 1 to 4 carbon atoms and lower alkoxy having from 1 to 4 carbon atoms; and where m is an integer of zero, one or two; including individual optically active isomers; racemic mixtures thereof; non-toxic pharmacologically-acceptable salts of the foregoing; and mixtures of the foregoing.

The term "lower alkanoyl", as employed herein, refers to a moiety having from 2 to 5 carbon atoms.

Various subscripts and symbols for chemical moieties, once defined herein, continue to have the same definition.

The compounds of formula 11 are advantageously derived from, or include residues of the structure of, the L-form of an amino acid, especially L-alanine, L-leucine, L-phenylalanine, L-sarcosine, L-serine, L-lysine, L-glutamine, L-tryptophane, L-cysteine, L-methionine, L-threonine, L-tyrosine or L-valine. Preferably, the amino acid will be selected from which $R_2$ will be hydrogen, methyl, isopropyl, isobutyl, hydroxy-methyl, cyclopentyl, phenyl, benzyl or 1H-indol-3-yl-methyl. L-alanine and L-valine are the preferred precursor amino acids, from which $R_2$ will be methyl and isopropyl, respectively.

It is preferred that Z have the structure

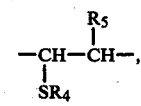

and most preferably the steric isomers denominated [R*, S*]. It is also preferred that $R_1$ be hydrogen; that $R_3$ be hydrogen; and that $R_5$ be methyl; and that $R_4$ be acetyl or propionyl. In respect of the ARYL moiety, it is preferred to have 2-naphthyl, 4-biphenyl, 5-indanyl, and especially phenyl or a substituted phenyl wherein the integer m is zero and $R_6$ is fluoro, chloro or bromo, phenoxy or halophenoxy. The divalent $R_8$ moiety preferably has 1 to 3 carbon atoms.

The novel compounds of the present invention may possess asymmetric carbon atoms (which are indicated by asterisks in the definition of Z) and thus may exist in diastereoisomeric forms. They can be produced as racemic mixtures or as individual enantiomers. The racemic mixtures can be resolved if desired by methods known to those skilled in the art, to obtain the respective individually optically active isomers. It is to be understood that the racemic mixtures and the individual isomers are encompassed within the scope of the subject matter claimed herein.

The novel substituted N-(ω-aroylpropionyl) derivatives of α-amino acids and esters thereof of the present invention are generally obtainable as white to yellow solids having characteristic absorption spectra or are obtained as white or yellow crystals with characteristic melting points and absorption spectra. They are generally soluble in many organic solvents such as lower alkanols, tetrahydrofuran, dioxane, chloroform and the like.

Also included within the purview of the present invention are the cationic salts of the compounds of formula (11) wherein $R_3$ is hydrogen. The useful pharmaceutically acceptable salts of the compounds wherein $R_3$ is hydrogen are those with pharmacologically acceptable metal cations, ammonium, amine cations, or quaternary ammonium cations. Preferred metal cations are those derived from the alkali metals, e.g., lithium, sodium and potassium, and from the alkaline earth metals, e.g., magnesium and calcium, although cationic forms of other metals, e.g., aluminum, copper, iron and in particular zinc, are within the scope of the invention. Pharmacologically acceptable amine cations are those derived from primary, secondary or tertiary amines such as amino-, di- or tri-methylamine, ethylamine, dibutylamine, tri-isopropylamine, N-methylhexylamine, decylamine, allylamine, cyclopentylamine, dicyclohexylamine, mono- or dibenzylamine, α- or β-phenylethylamine, ethylenediamine, and arylaliphatic amines containing up to and including 18 carbon atoms, as well as heterocyclic amines, e.g. piperidine, morpholine, pyrrolidine, piperazine and lower alkyl derivatives thereof, e.g., 1-methylpiperidine, 4-ethylmorpholine, 1-isopropylpyrrolidine, 1,4-dimethylpiperazine, and the like, as well as amines containing water-solubilizing or hydrophilic groups, e.g., mono-, di-, or tri-ethanolamine, N-butylethanolamine, 2-amino-1-butanol, 2-amino-2-ethyl-1,3-propanediol, tris(hydroxymethyl)aminomethane, N-phenylethanolamine, galactamine, N-methylglucosamine, ephedrine, phenylephrine, epinephrine, procaine, and the like. Examples of suitable pharmacologically acceptable quaternary ammonium cations are tetramethylammonium, tetraethylammonium, benzyltrimethylammonium, phenyltriethylammonium, and the like.

The novel compounds are useful in a method of ameliorating hypertension in a mammal, which process comprises administering to a mammal a therapeutically-effective amount of a compound represented by formula 11, including an optically active isomer, racemic mixtures thereof, non-toxic pharmacologically-acceptable salts thereof, and mixtures of the foregoing. The compounds N-[3-acetylthio-3-(4-bromobenzoyl)-propionyl]-L-valine and N-[3-acetylthio-3-(3-fluoro-4-methoxybenzoyl)propionyl]-L-alanine are preferred for use in such a process.

Biological Testing

Angiotensin II is a powerful vasoconstrictor agent that has been implicated as the main causative agent in the etiology or renovascular hypertension. Angiotensin II is formed from antiotensin II by the action of angiotensin-converting enzyme. Angiotensin I is a biologically inert decapeptide cleaved from the blood protein angiotensinogen by the action of the enzyme renin (Oparil, et al., New England J. of Med., Vol. 291, pages 389–457 (1974)). Angiotensinogen and renin are also biologically inert. Compounds which inhibit angiotensin-converting enzyme can therefore counteract the pressor effect of angiotensin I, since this is due only to its conversion to angiotensin II. These compounds can be used therapeutically in the treatment of forms of renovascular and malignant hypertension as well as other forms of angiotensin-dependent hypertension (Gavras, et al., New England J. of Med., Vol. 291, page 817 (1974)).

The novel compounds of this invention inhibit angiotensin-converting enzyme (hereinafter "ACE") and thus inhibit the conversion of angiotensin I to angiotensin II, and are therefore useful in ameliorating hypertension, especially angiotensin-related hypertension in various mammalian species.

The activity of the novel compounds of this invention as hypotensive agents was established in a system which measures their ability as angiotensin converting enzyme inhibitors, by utilizing a spectrophotometric assay of the compounds in vitro. The in vitro activity for inhibition of the angiotensin converting enzyme was measured by the method of D. W. Cushman and H. S. Cheung, Biochem. Pharmacol., Vol. 20, pages 1637–1648 (1972), using benzoyl-glycyl-histidyl-leucine as the substrate. The reaction mixture consisted of 50 μl. of potassium phosphate (500 mM., pH of 10.2), 30 μl. of sodium chloride (2500 mM.), 25 μl. of substrate (50 mM.), 30 to 50 μl. of the crude extract of ACE, 10 μl. of the test compound (2.5 mM.) or vehicle, and a suitable amount of distilled water to give a total volume of 250 μl. This reaction mixture was incubated for 30 minutes at 37° C. and the reaction was then terminated by the addition of 250 μl. of 1 N hydrochloric acid. The hippuric acid was then extracted with 1.5 ml. of ethyl acetate by vortex mixing for 15 seconds. After centrifugation, one ml. of the ethyl acetate layer was pipetted into a new tube and evaporated to dryness. The extracted hippuric acid was then dissolved in one ml. of water and the amount of this acid was then measured by its absorbance at 228 nm. The ACE was extracted from rabbit lung acetone powder (available from Pel-Freez Biol. Inc.) by blending 5 g. of the powder in 50 ml. of phosphate buffer (50 mM., pH of 8.3) and then centrifuging at 40,000 g. for 40 minutes. The supernatant was then kept at 5° C. and used as the enzyme source. The activity of the ACE inhibitor was calculated as the percent inhibition of ACE activity compared to the control value of that particular assay. A full dose-response inhibitory curve is then performed to determine the $IC_{50}$ value, which may be defined as the molar concentration of a compound that will inhibit the ACE activity by 50%. N-[3-Acetylthio-3-(4-bromobenzoyl)propionyl]-L-valine and N-[3-acetylthio-3-(3-fluoro-4-methoxybenzoyl)propionyl]-3-phenyl-L-alanine have been shown to be angiotensin converting enzyme inhibitors when tested as described above.

Another test which can be used to determine activity of hypotensive agents is by the measurement of the arterial blood pressure lowering effect of the compounds in the aorta-coarcted renal hypertensive rat. Male, Sprague-Dawley normotensive rats, weighing 300–325 g. (Charles River Breeding Lab. Inc., Wilmington, Mass.) are maintained on Purina Laboratory Chow and tap water ad libitum for 1–7 days before use. Hypertension is induced by complete ligation of the aorta between the origin of the renal arteries, according to the method of Rojo-Ortega, J. M. and Genest, J., A Method for Production of Experimental Hypertension in Rats, Can. J. Physiol. Pharmacol, Vol. 46, pages 883–885 (1968), with modifications of the surgical procedures. Thus, rats are anesthetized with methohexital sodium at 66 mg./kg. of body weight, intraperitoneally, and are laid on their right side. An incision is made just below the rib cage on their left side. With a cotton-tip swab, the fat is gently pushed back to expose the left kidney. The kidney is held gently between the thumb and the forefinger outside of the body cavity. The aorta is completely ligated between the origin of the renal arteries with a No. -000 silk suture. Care is taken to avoid the occlusion of the mesenteric artery. The wound is then closed in two layers using a 4-0 polyglycolic acid suture on the muscle and wound clips on the skin. The wound is then sprayed with No. 3 thimerosal aerosol. Following this surgery, the rats are returned to their cages and provided with Purina Laboratory Chow and Water ad libitum. Six days after the surgery, the conscious rats are restrained on rat boards with elastic tape. The neck area is locally anesthetized by subcutaneous infiltration of 2% lidocaine. After the trachea is cannulated and the rat respires spontaneously, the carotid artery is isolated and cannulated with a nylon catheter (inside diameter 0.015", outside diameter 0.030") which is connected to a Statham P23Gb pressure transducer—Gold Brush recorder (Model 2400) for monitoring blood pressure. The test compounds are dissolved in a small amount of ethanol and then diluted to the desired concentration with saline. Both the solution of the test compound and the vehicle alone are administered orally and run parallel in each experiment.

The novel compounds of the present invention are useful for lowering elevated blood pressure in mammals when administered in amounts ranging from about one mg. to about 1000 mg. per kilogram of body weight per day. A preferred dosage regimen for optimum results would be from about 10 mg. to about 300 mg. per kilogram of body weight per day. The dosage regimen may be adjusted to provide the optimum therapeutic response. For example, several divided doses may be administered daily or the dose may be proportionally reduced as indicated by the exigencies of the therapeutic situation. The active compounds are preferably administered orally but may be administered in any convenient manner such as by the intravenous, intramuscular or subcutaneous routes.

Compositions according to the present invention having the desired clarity, stability and adaptability for parenteral use are obtained by dissolving or suspending the active compound in a vehicle consisting of a polyhydric aliphatic alcohol or mixtures thereof. Especially satisfactory are glycerin, propylene glycol and polyethylene glycols. The polyethylene glycols consist of a mixture of non-volatile, normally liquid polyethylene glycols which are soluble in both water and organic liquids and which have molecular weights of from about 200 to 1500. Although the amount of active compound dissolved or suspended in the above vehicle may vary, the amount of active substance in the composition is such that dosage in the range of about 10 to 500 mg. of compound is obtained. Although various mixtures of the aforementioned non-volatile polyethylene glycols may be employed, it is preferred to use a mixture having an average molecular weight of from about 200 to about 400.

In addition to the active compound, the parenteral solutions or suspensions may also contain various preservatives which may be used to prevent bacterial and fungal contamination. The preservatives which may be used for these purposes are, for example, myristyl-picolinium chloride, benzalkonium chloride, phenethyl, alcohol, p-chlorophenyl-α-glycerol ether, methyl- and propyl-parabens and thimerosal. As a practical matter, it is also convenient to employ antioxidants, such as, for example, sodium bisulfite, sodium metabisulfite and sodium formaldehyde, sulfoxylate. Generally, from about 0.05 to about 0.2% concentrations of antioxidant are employed.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, suspensions, syrups, wafers and the like. Such compositions and preparations should contain at least 0.1% active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: a binder, such as gum tragacanth, acacia, corn starch or gelatin; excipients such as dicalcium phosphate; a disintegrating agent, such as corn starch, potato starch, alginic acid and the like; a lubricant such as magnesium stearate; and a sweetening agent, such as sucrose or lactose may be added, or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or suspension may contain the active compound, sucrose as a sweetening agent, methyl- and propyl-parabens as preservatives, a dye and flavoring such as cherry or orange flavor. Of course, any material used in preparing any dosage unit form should be pharmaceutically pure and substantially non-toxic in the amounts employed.

The novel compounds of formula 11, wherein Z is

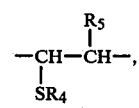

may be prepared in accordance with the following reaction scheme:

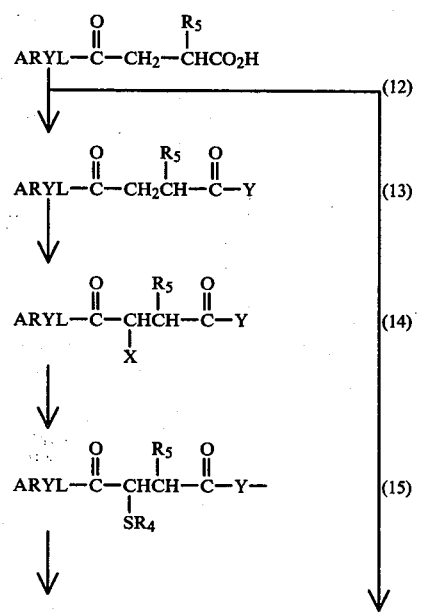

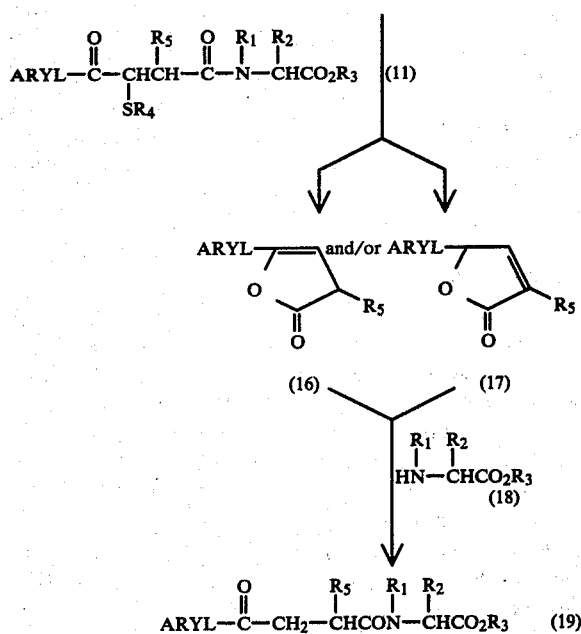

wherein X is selected from the class consisting essentially of chloro, bromo, iodo or —S—R'; wherein R' is a sulfur-protecting group, such as are known in the art, and which illustratively may be tert-butyl, benzyl, or p-methoxybenzyl; and Y is the carbonyl activating residue of a peptide coupling reagent or a moiety having a formula selected from the class consisting essentially of

wherein R" is, illustratively hydrogen, lower alkyl having 1-4 carbon atoms, phenyl, p-tolyl, p-methoxybenzyl, 2,4,6-trimethylbenzyl, trimethylsilyl, or 2-trimethylsilylethyl or a suitable carbonyl protecting group.

In accordance with the above reaction scheme, the carboxyl group of an appropriately substituted ω-aroylalkanoic acid (12) is converted to a carbonyl-activated derivative (13) or in accordance with the reaction scheme, derivatives (14) (where Y is hydroxyl) and (15) (where Y is also hydroxyl) are converted to carbonyl-activated derivatives. The carbonyl-activated derivatives (13), (14) and (15) are prepared by reaction of the free acids under standard reaction conditions for activating the carboxyl groups of N-protected amino acids. For example, mixed anhydrides are prepared in situ by treatment of the free acids with bases such as trialkylamines (e.g., triethylamine), N-methylmorpholine, pyridine, or N-methylpiperidine, to form the amine salts which are reacted with lower alkyl chloroformates such as ethyl chloroformate, t-butyl chloroformate, isobutyl chloroformate, benzyl chloroformate, or trityl chloroformate. Alternatively, the free acids can be reacted with N,N'-carbonyldiimidazole or a related peptide coupling reagent, such as N,N'-carbonyl-1,2,4-triazole, to form activated carbonyl derivatives. Derivatives where Y is O-hydroxysuccinimide or O-hydroxyphthalimide can be prepared by reaction of the free acids with N-hydroxysuccinimide or N-hydroxyphthalamide in the presence of a carbodiimide such as N,N-dicyclohexylcarbodiimide. Derivatives wherein Y is a residue of a peptide coupling reagent or an activated ester can be reacted with an α-aminoacid or a derivative of an α-aminoacid under conventional coupling conditions.

The amides are obtained by reacting an acid halide of a compound of formula (12) or preferably a carbonyl activated derivative (13) with an α-aminoacid of formula (19) wherein $R_3$ is hydrogen, or an ester thereof such as an alkyl $C_1$-$C_4$ alkyl ester, a benzyl ester, 2,4,6-trimethylbenzyl ester or a derivative having a carboxyl protecting group, which group is removed in a later step. The reaction conditions for the formation of the carboxyl activated derivatives and conditions for coupling to α-aminoacid derivatives, such as time, temperature, solvents, etc., are known in the art. In general, the reactions are carried out at 0° C. to 50° C. in solvents such as tetrahydrofuran, dioxane, N,N-dimethylformamide, dimethylsulfoxide, toluene, or acetonitrile for 1-24 hours.

Further elucidation of the meaning of the terms employed herein is afforded by the following table wherein typical peptide coupling reagents are listed in the left column and the corresponding carbonyl activating residues are listed in the right column:

| Reagent | —Y |
|---|---|
| N—hydroxyphthalimide | (phthalimide structure) |
| dicyclohexylcarbodiimide | (dicyclohexyl structure) |
| N,N'—carbonyldiimidazole | (imidazole structure) |
| benzyl chloroformate | —O—C(=O)—CH$_2$—(phenyl) |
| N—hydroxysuccinimide | (succinimide structure) |
| activated ester | —S—Aryl |

| Reagent | —Y |
|---|---|
| -continued | |
| mixed anhydride | $-O-\overset{\overset{O}{\|}}{C}-C(CH_3)_3$ |
| | $-\overset{\overset{O}{\|}}{C}-O-Alkyl$ |
| | $-SO_2-Aryl$ |

Numerous other peptide coupling reagents are available and known to the art, such as unsaturated ethers, α-chlorovinyl ethyl ether, ethoxyacetylene, ketenimines and ketenes, ynamines, acyloxyphosphonium ions, EEDQ, silicon tetrachloride, and 1,2-oxazolium salts. These all provide a carbonyl activating residue (Y) and may be readily used for the conversion of compounds of formula (14) to compounds of formula (15) when Y is to be a carbonyl activating residue of a peptide coupling reagent. The reaction conditions for such conversions are known in the art; see for example, an article in SYNTHESIS, September 1972, pages 453-463 by Klausner & Bodansky.

Alternatively, 3-(aroyl)propionic acids of formula (12) may be cyclized to 5-aryl-2-(3H)-furanones of formula (16) or 5-aryl-2(5H)-furanones of formula (17) which react with α-aminoacid derivatives of formula (18) to give the intermediates of formula (19). The cyclization of acids of formula (12) may be carried out in lower alkanoic acid anhydrides or in inert solvents such as benzene, toluene, xylene and the like in the presence of one to three mols of a lower alkanoic acid anhydride. Coupling of furanones of formulas (16) or (17) with α-aminoacid derivatives of formula (18) may be carried out in the presence of one mol of a trialkylamine such as trimethylamine or triethylamine, in a solvent such as acetonitrile or dioxane for 10-48 hours to give compounds of formula (19).

The conversion of the intermediates of formula (13) to the corresponding 3-(X-substituted) propionic acid derivative of formula (14) is readily achieved by conventional methods. For example, the chloro, bromo and iodo derivatives may be prepared by treating a compound of formulas (13) or (19) with a halogenating agent such as chlorine, bromine, or N-iodosuccinimide, in a solvent such as chloroform, carbon tetrachloride, acetic acid or dioxane at 25°-75° C. for 12-14 hours. Those compounds wherein X is —S—R' may be obtained from the halo derivatives by treatment with an alkali metal mercaptide under standard conditions. If desired, the ω-aroylalkanoic acids of formula (12) may be coupled to an α-aminoacid derivative having the formula

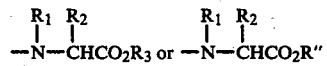

to produce intermediates having the formula (13) which are then converted to products of formula (11) through intermediates of formulas (14) and (15). Alternatively, intermediates of formula (13) wherein Y is a carboxyl protecting group may be converted to intermediates of formulas (14) and (15), at which point the protecting group may be removed and the intermediates of formula (14) or (15), wherein Y is hydroxyl, can be coupled to an α-aminoacid or a derivative thereof.

The ω-aroylalkanoic acids of formula (12), wherein $R_5$ is other than hydrogen, have an asymmetric carbon atom and the D and L isomers may be prepared by resolution of the racemic mixture. Activation of the carboxyl group of the resolved isomers then gives compounds of formula (13) wherein the carbon atom bearing the $R_5$ group has either the D or the L configuration. Conversion of the resolved compounds of formula (13) to the reactive intermediates of formula (14) gives compounds which are diastereoisomers. Each diastereomisomer may then be converted to compounds of formula (15) as shown in the reaction scheme. Alternatively, racemic compounds of formula (12) wherein $R_5$ is lower alkyl may be coupled to α-aminoacid derivatives to give compounds of formula (13) which exist as diastereoisomeric forms and may be separated by convention means. For example, the diastereoisomeric forms may be separated by preferential crystallization of one diastereoisomer and isolation of the other diastereoisomer from the mother liquors. In this manner diastereoisomeric forms of compounds of formula (14) may be prepared and converted to the compounds of formula (11) which are inhibitors of the angiotensin converting enzyme.

The reactive intermediates of formula (14) can be reacted with the anion of a thioacid of formula

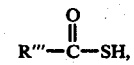

wherein R''' is phenyl or an alkyl having up to 3 carbon atoms. Suitable anions of thioacids and thiolating reagents useful in the displacement reaction are those from alkali metals, especially potassium or sodium ions, alkaline earth metals such as calcium and magnesium, and organic bases such as ammonia or a trialkylamine. Removal of the acyl group by reaction with hydroxylamine, ammonium hydroxide or dilute inorganic bases gives the compounds of formula (11) wherein $R_4$ is hydrogen.

Under appropriate conditions intermediates of formulas (14) and (15), wherein X is —S—R' and Y is

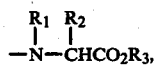

may be converted directly to products of formula (11), wherein $R_4$ is hydrogen, by removal of a thio protecting group. For example, derivatives wherein R is a thio protecting group such as t-butyl, p-methoxybenzyl, $C_6H_5CH_2O_2CS-$ and the like may be deblocked under acidic conditions (HBr—HOAc, $CF_3CO_2H$, $(CF_3CO_2)_2Hg$ or the like) known to the art.

Derivatives of compounds of formula (15) wherein Y is

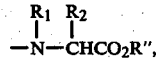

and R" is a carboxyl protecting group, may be converted to products of formula (11) (when $R_3$ is hydrogen) by removal of the carboxyl protecting group under conventional conditions. In general, carboxyl protecting groups which are removed under acidic conditions are preferred. For example, 2,4,6-trimethylbenzylesters are cleaved by treatment with anhydrous hydrogen bromide in acetic acid at 0°–50° C. for 1–24 hours. Trimethylsilyl and 2-trimethylsilylethyl are removed under conventional conditions known to the art. The reactions illustrated in the reaction scheme may be carried out with esters (where $R_3$ is lower alkyl) to give the products of formula (11) wherein $R_3$ is lower alkyl. In the products of formula (11) (wherein $R_3$ is replaced by a carboxyl protecting group such as 2,4,6-trimethylbenzyl), the ester group may be removed with anhydrous hydrogen bromide in acetic acid to give a free acid compound (where $R_3$ is hydrogen) of formula (11).

The novel compounds of formula (11)

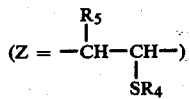

may be prepared in accordance with the following reaction scheme:

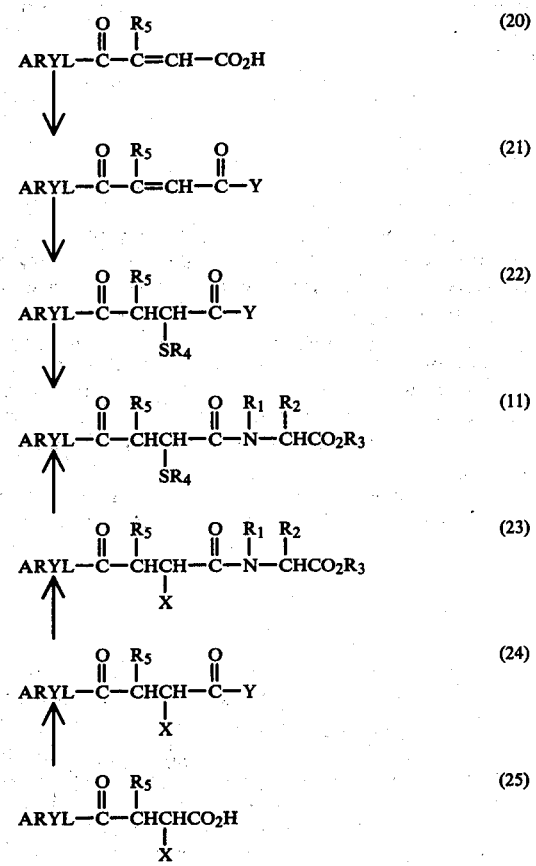

In accordance with the above reaction scheme, an appropriately substituted-3-(aroyl)acrylic acid of formula (20) or a 3-(X-substituted)propionic acid of formula (25) is converted to a carbonyl activated derivative of formula (21), or formula (24), respectively. The reaction conditions for the formation of such carbonyl activated derivatives, such as time, temperature, and solvent media, are known in the art and are referred to above. The carboxyl activated derivatives of formulas (21), (22) and (24) are prepared by treatment of a free acid of formula (20) or formula (24) with peptide coupling reagents as hereinbefore discussed (see table for carbonyl activating residues).

Derivatives of formulas (21), (22) and (24) wherein Y is a residue of a peptide coupling reagent or an activated ester can be reacted with an α-aminoacid or an α-aminoacid derivative of the formulae:

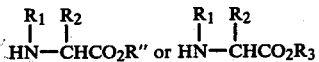

to give intermediates of formulas (21) and (24), respectively.

The intermediates of formulas (21) or (24) can be reacted with a thiolating reagent which gives the products of formula (11) directly, or intermediates of formulas (22) or (23), which are convertible into products of formula (11). Thiolating reagents add 1,4 to the ketone carbonyl of intermediates of formulas (20) and (21). Suitable thiolating reagents are $H_2S$, $H-S-C(CH_3)_3$ and $HSR_4$. Preferred reagents are hydrogen sulfide or a thiolating agents of the formula

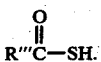

Preferred conditions for the addition of a thiolating reagent are reaction in an inert solvent such as chloroform, dichloromethane, carbon tetrachloride, dimethylformamide, tetrahydrofuran, dioxane, acetonitrile, toluene or lower alkanols at 0°–10° C. for one to 24 hours.

The intermediates of formulas (25), and (24) and (23) can be reacted with the anion of a thiolating reagent. Suitable thiolating reagents are $Na_2S$, NaHS and anions of a thiolating reagents of the formulae $HSC(CH_3)_3$ and

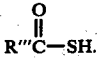

Conversion of compounds of formulas (22) and (24), wherein Y is a group of the formula

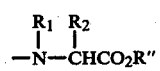

is carried out by removal of the protecting group to give products of formula (11) wherein $R_3$ is hydrogen. Carboxyl protecting groups which are removed under acidic conditions are preferred. The reactions illustrated in the reaction scheme may be carried out with esters of α-aminoacid derivatives to give products of formula (11) wherein $R_3$ is lower alkyl. Derivatives which contain a thio protecting group may be converted to products of formula (11) wherein $R_4$ is hydrogen by removing the protecting group under conventional conditions.

The invention will be described in greater detail in conjunction with the following specific examples.

EXAMPLE 1

N-[3-Acetylthio-3-(4-bromobenzoyl)propionyl]-L-valine

A solution of 41.2 g. (0.2 mol) of N,N-dicyclohexylcarbodiimide in 150 ml. of dioxane was added to a mixture of 51.4 g. (0.2 mol) of 3-(4-bromobenzoyl)propionic acid and 23.0 g. (0.2 mol) of N-hydroxysuccinimide in 250 ml. of dioxane. The mixture was stirred for 4 hours at room temperature and then filtered. The filtrate was concentrated in vacuo and the residue triturated with hexane. The solid was filtered and dissolved in 130 ml. of dichloromethane. The dichloromethane solution was diluted with 120 ml. of hexane and chilled, producing 45.0 g. of the N-hydroxysuccinimide ester of 3-(4-bromobenzoyl)propionic acid as off-white crystals, m.p. 129°–131° C.

The preceding compound (10.6 g.; 0.03 mol) was added to a solution of 5.27 g. (0.045 mol) of L-valine and 7.56 g. (0.09 mol) of sodium bicarbonate in 140 ml. of water. Dioxane (20 ml.) was added and the mixture stirred for 48 hours at room temperature. The mixture was filtered and the filtrate acidified with concentrated hydrochloric acid. The solid phase was separated by filtration and washed with water, yielding 9.53 g. of cream colored crystals. Recrystallization from 100 ml. of methanol-water (1:1) produced 8.64 g. of N-[3-(4-bromobenzoyl)propionyl]-L-valine as white crystals, m.p. 160°–162° C.

To the preceding compound (3.56 g.; 0.01 mol) in 25 ml. of acetic acid there was added 0.011 mol of bromine. The mixture was stirred at room temperature until the color of bromine disappeared. Then the solvent was removed in vacuo. The residue was dissolved in dichloromethane and the solution washed with water and dried over magnesium sulfate. The solvent was removed, and N-[3-bromo-3-(4-bromobenzoyl)propionyl)]-L-valine was recovered.

The preceding compound was dissolved in dry acetonitrile and 0.01 mol of potassium thioacetate was added. The mixture was stirred for 8 hours and several drops of acetic acid were added. The solvent was removed and the residue purified by chromatography on silica gel with solvent hexane-ethyl acetate (7:3) containing 2% acetic acid to produce N-[3-acetylthio-3-(4-bromobenzoyl)propionyl]-L-valine as a glass.

EXAMPLE 2

N-[3-Acetylthio-3-(4-bromobenzoyl)propionyl]-L-alanine

Substitution of L-alanine (0.03 mol) for L-valine in Example 1 produced N-[3-(4-bromobenzoyl)propionyl)]-L-alanine which, upon recrystallization from methanol-water, gave 5.53 g. of white crystals, m.p. 110°–113° C. Reaction of the preceding compound with bromine in acetic acid can give N-(3-bromo-(4-bromobenzoyl)propionyl)-L-alanine, which can be reacted with potassium thioacetate as analogously described in Example 1 to product N-[3-acetylthio-3-(4-bromobenzoyl)propionyl]-L-alanine as a glass.

EXAMPLE 3

N-[3-Acetylthio-3-(4-bromobenzoyl)propionyl]-L-glycine

Reaction of L-glycine (3.38 g.; 0.03 mol) with the N-hydroxysuccinimide ester of 3-(4-bromobenzoyl)propionic acid as described for Example 1 gave 7.89 g. of solid which was recrystallized from methanol-water to give 6.39 g. of N-[3-(4-bromobenzoyl)propionyl]-L-glycine as white crystals, m.p. 151°–153° C.

As in Example 1, the preceding compound can be converted to N-[3-acetylthio-3-(4-bromobenzoyl)propionyl]-L-glycine.

EXAMPLE 4

N-[3-Acetylthio-3-(4-bromobenzoyl)priopionyl]-L-phenylalanine

Reaction of 7.47 g. (0.03 mol) of L-phenylalanine with 10.6 g. (0.03 mol) of the N-hydroxysuccinimide ester of 3-(4-bromobenzoyl)propionic acid as described in Example 1 gave 11.8 g. of solid. The solid was dissolved in 40 ml. of acetic acid and 160 ml. of hexane added to produce 8.70 g. of white crystals, m.p. 135°–138° C. Recrystallization from methanol-water gave 7.67 g. of N-[3-(4-bromobenzoyl)propionyl]-L-phenylalanine. As described in Example 1, the preceding compound can be converted to N-[3-acetylthio-3-(4-bromobenzoyl)priopionyl]-L-phenylalanine.

EXAMPLE 5

N-[3-Acetylthio-3-(4-methoxybenzoyl)propionyl]-L-valine

To a mixture of 18.72 g. (0.09 mol) of 3-(4-methoxybenzoyl)propionic acid and 10.35 g. (0.09 mol) of N-hydroxysuccinimide in 100 ml. of dioxane there was added a solution of 18.54 g. (0.09 mol) of N,N-dicyclohexylcarbodiimide in 80 ml. of dioxane. After stirring at room temperature for 18 hours, the mixture was filtered and the filtrate concentrated in vacuo to produce a gum. The gum was triturated with ether to produce 28 g. of solid. The solid was dissolved in 130 ml. of dichloromethane and the solution diluted with 130 ml. of petroleum ether (b.p. 30°–60° C.). Chilling and filtering gave 20.5 g. of the N-hydroxysuccinimide ester of 3-(4-methoxybenzoyl)propionic acid as white crystals, m.p. 128°–131° C.

(A) The preceding compound (4.58 g.; 0.015 mol) was added to a solution of 2.57 g. (0.022 mol) of L-valine and 3.7 g. (0.044 mol) of sodium bicarbonate in 70 ml. of water containing 10 ml. of dioxane. The mixture was stirred at room temperature for 18 hours and filtered. The filtrate was chilled and acidified by the dropwise addition of concentrated hydrochloric acid. Filtration gave a solid which was washed with water to produce 4.27 g. of crystals, m.p. 160°–163° C. Recrystallization from methanol-water gave 2.93 g. of N-[3-(4-methoxybenzoyl)propionyl]-L-valine as crystals, m.p. 166°–168° C.

(B) The preceding compound (0.005 mol) can be dissolved in acetic acid and 0.005 mol of bromine added. The mixture should be stirred 16 hours at room temperature and the solvent removed in vacuo. The residue, dissolved in dichloromethane, can be washed with water. The organic solution can be dried over magnesium sulfate and filtered. To the filtrate can be added 0.0055 mol of potassium thioacetate. The mixture can be stirred for 10 hours, then several drops of acetic acid added. The mixture can be washed with water and dried over magnesium sulfate and the solvent removed in vacuo to produce N-[3-acetylthio-3-(4-methoxybenzoyl)propionyl]-L-valine.

EXAMPLE 6

N-[3-Acetylthio-3-(4-methoxybenzoyl)propionyl]-L-alanine

Substituting L-alanine for L-valine in the procedure of Example 5(A) produced N-[3-(4-methoxybenzoyl)-propionyl]-L-alanine, m.p. 100°–102° C. By substituting the preceding compound for N-[3-(4-methoxybenzoyl)- propionyl]-L-valine in the procedure of Example 5(B), N-[3-acetylthio-3-(4-methoxybenzoyl)propionyl]-L-alanine can be obtained.

EXAMPLE 7
N-[3-Acetylthio-3-(4-methoxybenzoyl)propionyl]-L-phenylalanine

N-[3-(4-methoxybenzoyl)propionyl]-L-phenylalanine, m.p. 131°–133° C. is prepared as described for the preparation of N-[3-(4-methoxybenzoyl)propionyl)]-L-valine in Example 5(A).

By substituting N-[3-(4-methoxybenzoyl)propionyl)]-L-phenylalanine in the procedure of Example 5(B), one can obtain N-[3-acetylthio-3-(4-methoxybenzoyl)propionyl]-L-phenylalanine.

EXAMPLE 8
N-[3-Acetylthio-3-(4-methoxybenzoyl)propionyl]-L-glycine

By substituting N-[3-(4-methoxybenzoyl)propionyl]-L-glycine, m.p. 137°–138° C. (prepared as described for the L-valine derivative of Example 5(A)) for L-valine in the procedure of Example 5(B), one can obtain N-[3-acetylthio-3-(4-methoxybenzoyl)propionyl]-L-glycine.

EXAMPLE 9
N-[3-Acetylthio-3-(4-bromobenzoyl)propionyl]-L-leucine

Substitution of L-leucine for L-valine in the procedure of Example 1 produces N-[3-acetylthio-3-(4-bromobenzoyl)propionyl]-L-leucine.

EXAMPLE 10
N-[3-Acetylthio-3-(4-bromobenzoyl)propionyl]-L-sarcosine

Substitution of L-sarcosine for L-valine in the procedure of Example 1 produces N-[3-acetylthio-3-(4-bromobenzoyl)propionyl]-L-sarcosine.

EXAMPLE 11
N-[3-Acetylthio-3-(4-bromobenzoyl)propionyl]-L-methionine

Substitution of L-methionine for L-valine in the procedure of Example 1 produces N-[3-acetylthio-3-(4-bromobenzoyl)propionyl]-L-methionine.

EXAMPLE 12
N-[3-Acetylthio-3-(4-bromobenzoyl)propionyl]-L-tryptophan

Substitution of L-tryptophan for L-valine in the procedure of Example 1 produces N-[3-acetylthio-3-(4-bromobenzoyl)propionyl]-L-tryptophan.

EXAMPLE 13
N-[3-Acetylthio-3-(4-bromobenzoyl)propionyl]-S-methyl-L-cysteine

Substitution of S-methyl-L-cysteine for L-valine in the procedure of Example 1 produces N-[3-acetylthio-3-(4-bromobenzoyl)propionyl]-S-methyl-L-cysteine.

EXAMPLE 14
N-[3-Acetylthio-3-(4-bromobenzoyl)propionyl]-L-glutamine

Substitution of L-glutamine for L-valine in the procedure of Example 1 produces N-[3-acetylthio-3-(4-bromobenzoyl)propionyl]-L-glutamine.

EXAMPLE 15
N-[3-Acetylthio-3-(4-methoxybenzoyl)propionyl]-L-leucine

Substitution of L-leucine for L-valine in the procedure of Example 5 produces N-[3-acetylthio-3-(4-methoxybenzoyl)propionyl]-L-leucine.

EXAMPLE 16
N-[3-Acetylthio-3-(4-methoxybenzoyl)propionyl]-L-sarcosine

Substitution of L-sarcosine for L-valine in the procedure of Example 5 produces N-[3-acetylthio-3-(4-methoxybenzoyl)propionyl]-L-sarcosine.

EXAMPLE 17
N-[3-Acetylthio-3-(4-methoxybenzoyl)propionyl]-L-methionine

Substitution of L-methionine for L-valine in the procedure of Example 5 produces N-[3-acetylthio-3-(4-methoxybenzoyl)propionyl]-L-methionine.

EXAMPLE 18
N-[3-Acetylthio-3-(4-methoxybenzoyl)propionyl]-L-tryptophan

Substitution of L-tryptophan for L-valine in the procedure of Example 5 produces N-[3-acetylthio-3-(4-methoxybenzoyl)propionyl]-L-tryptophan.

EXAMPLE 19
N-[3-Acetylthio-3-(4-methoxybenzoyl)propionyl]-S-methyl-L-cysteine Substitution of S-methyl-L-cysteine for L-valine in the procedure of Example 5 produces N-[3-acetylthio-3-(4-methoxybenzoyl)propionyl]-S-methyl-L-cysteine.

EXAMPLE 20
N-[3-Acetylthio-3-(4-methoxybenzoyl)propionyl]-L-glutamine

Substitution of L-glutamine for L-valine in the procedure of Example 5 produces N-[3-acetylthio-3-(4-methoxybenzoyl)propionyl]-L-glutamine.

EXAMPLE 21
N-[3-Acetylthio-3-(3-fluoro-4-methoxybenzoyl)propionyl]-L-valine

To a mixture of 27.0 g. (0.12 mol) of 3-(3-fluoro-4-methoxybenzoyl)propionic acid and 13.8 g. (0.12 mol) of N-hydroxysuccinimide in 140 ml. of dioxane, there was added a solution of 24.7 g. (0.12 mol) of N,N-dicyclohexylcarbodiimide in 100 ml. of dioxane. The mixture as stirred at room temperature for 18 hours and filtered. The filtrate was concentrated in vacuo, producing a gum. Trituration with ether gave 36.1 g. of white crystals, m.p. 119°–126° C. The solid was dissolved in 170 ml. of dichloromethane and 170 ml. of petroleum ether (bp. 30°-60° C.) was added. Chilling and filtering gave 28.5 g. of the N-hydroxysuccinimide ester of 3-(3-fluoro-4-methoxybenzoyl)propionic acid as white crystals, m.p. 127°-133° C.

The preceding compound (7.1 g.; 0.22 mol) was added to a solution of 3.86 g. (0.033 mol) of L-valine and 5.54 g. (0.066 mol) of sodium bicarbonate in 100 ml. of water containing 10 ml. of tetrahydrofuran. The mixture was stirred at room temperature for 18 hours and filtered. The filtrate was chilled (ice bath) and acidified with concentrated hydrochloric acid. The mixture was filtered and the solid washed with water to give crystals, m.p. 140°-144° C. Recrystallization from methanol-water gave 5.0 g. of N-[3-(3-fluoro-4-methoxybenzoyl)-propionyl]-L-valine as white crystals, m.p. 153°-155° C.

To the preceding compound (0.01 mol) in 20 ml. of acetic acid was added (0.01 mol) of bromine. The mixture was stirred for 16 hours, then the solvent removed in vacuo. The residue was dissolved in dichloromethane and copiously washed with water. The solution was dried over magnesium sulfate and 0.01 mol of potassium thioacetate was added. The mixture was stirred for 16 hours and several drops of acetic acid were added. The mixture was washed with water and dried over magnesium sulfate. The solvent was removed in vacuo to give N-[3-acetylthio-3-(3-fluoro-4-methoxybenzoyl)propionyl]-L-valine as a glass. Further purification can be carried out by chromatography on silica gel.

EXAMPLE 22

N-[3-Acetylthio-3-(3-fluoro-4-methoxybenzoyl)propionyl]-L-alanine

Substituting L-alanine for L-valine in the procedure of Example 21 gave N-[3-(3-fluoro-4-methoxybenzoyl)-propionyl]-L-alanine, m.p. 126°-128° C. The preceding compound can be converted to N-[3-acetylthio-3-(3-fluoro-4-methoxybenzoyl)propionyl]-L-alanine by the procedure described in Example 21.

EXAMPLE 23

N-[3-Acetylthio-3-(3-fluoro-4-methoxybenzoyl)propionyl]-L-phenylalanine

By substituting N-[3-(3-fluoro-4-methoxybenzoyl)-propionyl]-L-phenylalanine (prepared as described for the L-valine derivative of Example 21), m.p. 140°-146° C. for N-[3-(3-fluoro-4-methoxybenzoyl)propionyl-L-valine in the procedure of Example 21, one can obtain a glass which can be chromatographed over silica gel with hexane-ethyl acetate (4:1) containing 2% acetic acid to obtain N-[3-acetylthio-3-(3-fluoro-4-methoxybenzoyl)propionyl]-L-phenylalanine as a glass.

EXAMPLE 24

N-[3-Acetylthio-3-(3-fluoro-4-methoxybenzoyl)propionyl]-L-glycine

Substituting L-glycine for L-valine in the procedure of Example 21 gave N-[3-(3-fluoro-4-methoxybenzoyl)-propionyl]-L-glycine, m.p. 167°-169° C. By substituting the preceding compound for N-[3-(3-fluoro-4-methoxybenzoyl)propionyl]-L-valine in the procedure of Example 21, one can obtain N-[3-acetylthio-3-(3-fluoro-4-methoxybenzoyl)propionyl]-L-glycine.

EXAMPLE 25

N-[3-Acetylthio-3-(3-fluoro-4-methoxybenzoyl)propionyl]-L-leucine

Substitution of L-leucine for L-valine in the procedure of Example 21 produces N-[3-acetylthio-3-(3-fluoro-4-methoxybenzoyl)propionyl]-L-leucine.

EXAMPLE 26

N-[3-Acetylthio-3-(3-fluoro-4-methoxybenzoyl)propionyl]-L-sarcosine

Substitution of L-sarcosine for L-valine in the procedure of Example 21 produces N-[3-acetylthio-3-(3-fluoro-4-methoxybenzoyl)propionyl]-L-sarcosine.

EXAMPLE 27

N-[3-Acetylthio-3-(3-fluoro-4-methoxybenzoyl)propionyl]-L-methionine

Substitution of L-methionine for L-valine in the procedure of Example 21 produces N-[3-acetylthio-3-(3-fluoro-4-methoxybenzoyl)propionyl]-L-methionine.

EXAMPLE 28

N-[3-Acetylthio-3-(3-fluoro-4-methoxybenzoyl)propionyl]-L-tryptophan

Substitution of L-tryptophan for L-valine in the procedure of Example 21 produces N-[3-acetylthio-3-(3-fluoro-4-methoxybenzoyl)propionyl]-L-tryptophan.

EXAMPLE 29

N-[3-Acetylthio-3-(3-fluoro-4-methoxybenzoyl)propionyl]-S-methyl-L-cysteine

Substitution of S-methyl-L-cysteine for L-valine in the procedure of Example 21 produces N-[3-acetylthio-3-(3-fluoro-4-methoxybenzoyl)propionyl]-S-methyl-L-cysteine.

EXAMPLE 30

N-[3-Acetylthio-3-(3-fluoro-4-methoxybenzoyl)propionyl]-L-glutamine

Substitution of L-glutamine for L-valine in the procedure of Example 21 produces N-[3-acetylthio-3-(3-fluoro-4-methoxybenzoyl)propionyl]-L-glutamine.

EXAMPLE 31

N-[3-Acetylthio-3-(2-naphthoyl)propionyl]-L-valine

Substitution of 3-(2-naphthoyl)propionic acid for 3-(4-bromobenzoyl)propionic acid in the procedure of Example 1 gave the N-hydroxysuccinimide ester of 3-(2-naphthoyl)propionic acid, m.p. 153°-160° C.

Substitution of the preceding compound for the N-hydroxysuccinimide ester of 3-(4-bromobenzoyl)propionic acid in the procedure of Example 1 produces N-[3-acetylthio-3-(2-naphthoyl)propionyl]-L-valine.

EXAMPLE 32

N-[3-Acetylthio-3-(3-fluorobenzoyl)propionyl]-L-valine

Substitution of 3-(3-fluorobenzoyl)propionic acid for 3-(4-bromobenzoyl)propionic acid in the procedure of Example 1 produces N-[3-acetylthio-3-(3-fluorobenzoyl)propionyl]-L-valine.

EXAMPLE 33

N-[3-Acetylthio-3-(3-chlorobenzoyl)propionyl]-L-valine

Substitution of 3-(3-chlorobenzoyl)propionic acid for 3-(4-bromobenzoyl)propionic acid in the procedure of Example 1 produces N-[3-acetylthio-3-(3-chlorobenzoyl)propionyl]-L-valine.

EXAMPLE 34

N-[3-Acetylthio-3-(1-napthoyl)propionyl]-L-phenylalanine

Substitution of 3-(1-naphthoyl)propionic acid for 3-(4-bromobenzoyl)propionic acid and L-phenylalanine for L-valine in the procedure of Example 1 produces N-[3-acetylthio-3-(1-napthoyl)propionyl]-L-phenylalanine.

EXAMPLE 35

N-[3-Acetylthio-3-(2-naphthoyl)propionyl]-L-alanine

Substitution of 3-(2-napthoyl)propionic acid for 3-(4-bromobenzoyl)propionic acid and L-alanine for L-valine in the procedure of Example 1 produces N-[3-acetylthio-3-(2-naphthoyl)propionyl]-L-alanine.

EXAMPLE 36

N-[3-Acetylthio-3-(4-tert-butylbenzoyl)propionyl]-L-sarcosine

Substitution of 3-(4-tert-butylbenzoyl)propionic acid for 3-(4-bromobenzoyl)propionic acid and L-sarcosine for L-valine in the procedure of Example 1 produces N-[3-acetylthio-3-(4-tert-butylbenzoyl)propionyl]-L-sarcosine.

EXAMPLE 37

N-[3-Acetylthio-3-(3,4-dichlorobenzoyl)propionyl]-L-alanine

Substitution of 3-(3,4-dichlorobenzoyl)propionic acid for 3-(4-bromobenzoyl)propionic acid and L-alanine for L-valine in the procedure of Example 1 produces N-[3-acetylthio-3-(3,4-dichlorobenzoyl)propionyl]-L-alanine.

EXAMPLE 38

N-[3-Acetylthio-3-(5-indanylcarbonyl)propionyl]-L-glycine

Substitution of 3-(5-indanylcarbonyl)propionic acid for 3-(4-bromobenzoyl)propionic acid and L-glycine for L-valine in the procedure of Example 1 produces N-[3-acetylthio-3-(5-indanylcarbonyl)propionyl]-L-glycine.

EXAMPLE 39

N-[3-Acetylthio-3-[4-(4-chlorophenoxy)benzoyl]propionyl]-L-phenylalanine

Substitution of 3-[4-(4-chlorophenoxy)benzoyl]propionic acid for 3-(4-bromobenzoyl)propionic acid and L-phenylalanine for L-valine in the procedure of Example 1 produces N-[3-acetylthio-3-[4-(4-chlorophenoxy)benzoyl]propionyl]-L-phenylalanine.

EXAMPLE 40

N-[3-Acetylthio-3-(benzoyl)propionyl]-L-valine

To a partial solution of 53.4 g. of 3-benzoylpropionic acid and 34.5 g. of N-hydroxysuccinimide in 325 ml. of dioxane, there was added a solution of 61.8 g. of N,N-dicyclohexylcarbodiimide in 225 ml. of dioxane. The mixture was stirred at room temperature for 18 hours, then filtered. The filtrate was concentrated in vacuo. The residue was triturated with hexane and filtered. The solid was dissolved in 700 ml. of dichloromethane and 700 ml. of hexane was added. Chilling and filtering gave a solid which was washed with 250 ml. of dichloromethane-hexane (1:1) to give the N-hydroxysuccinimide ester of 3-benzoylpropionic acid as white crystals, m.p. 130°–132° C.

The preceding compound (9.91 g.; 0.036 mol) was added to a solution of 6.09 g. (0.052 mol) of L-valine and 9.24 g. (0.12 mol) of sodium bicarbonate in 80 ml. of water. Dioxane (100 ml.) was added and the mixture stirred at room temperature for 18 hours. The mixture was concentrated to dryness in vacuo and the residue partitioned between dichloromethane and dilute hydrochloric acid. The organic layer was dried over anhydrous sodium sulfate and concentrated in vacuo. The residue was crystallized from dichloromethane-hexane to give 9.0 g. of crystals, m.p. 117°–118° C.

Recrystallization from dichloromethane-hexane gave N-(3-benzoylpropionyl)-L-valine as white crystals, m.p. 118°–120° C.

To the preceding compound (0.01 mol) in 15 ml. of acetic acid, one can add 0.01 mol of bromine. The reaction mixture can be stirred for 16 hours, then the solvent removed in vacuo. The residue in dichloromethane can be washed with water. The organic layer can be dried over magnesium sulfate, and 0.01 mol of potassium thioacetate can be added. After stirring 18 hours, one ml. of acetic acid can be added. Then the mixture can be washed with water and dried over magnesium sulfate. The solvent can be removed in order to obtain N-[3-acetylthio-3-(benzoyl)propionyl]-L-valine as a glass.

EXAMPLE 41

N-[3-Acetylthio-3-(benzoyl)propionyl]-L-alanine

To a solution of 4.64 g. (0.052 mol) of L-alanine and 9.24 g. (0.012 mol) of sodium bicarbonate in 80 ml. of water there was added 9.91 g. (0.036 mol) of the N-hydroxysuccinimide ester of 3-benzoylpropionic acid. Dioxane (100 ml.) was added and the mixture stirred at room temperature for 18 hours. The procedure as described for Example 40 gave 6.0 g. of N-(3-benzoylpropionyl)-L-alanine as white crystals, m.p. 113°–116° C.

By substituting the preceding compound for N-(3-benzoylpropionyl)-L-valine in the procedure of Example 40, one can obtain N-[3-acetylthio-3-(benzoyl)propionyl]-L-alanine.

EXAMPLE 42

N-[3-Acetylthio-3-(benzoyl)propionyl]-L-glycine

Substitution of L-glycine for L-valine in the procedure of Example 40 gave N-(3-benzoylpropionyl)-L-glycine as tan crystals, m.p. 108°–109° C.

By substituting the preceding compound for N-(3-benzoylpropionyl)-L-valine in the procedure of Example 40, one can obtain N-[3-acetylthio-3-(benzoyl)propionyl]-L-glycine.

EXAMPLE 43

N-[3-Acetylthio-3-(benzoyl)propionyl]-L-phenylalanine

By substituting N-(3-benzoylpropionyl)-L-phenylalanine, m.p. 110°–112° C. for N-(3-benzoylpropionyl)-L-valine in the procedure of Example 40, one can obtain N-[3-acetylthio-3-(benzoyl)propionyl]-L-phenylalanine.

EXAMPLE 44

N-[3-Acetylthio-3-(4-fluorobenzoyl)propionyl]-L-valine

To a solution of 3.05 g. (0.026 mol) of L-valine and 4.62 g. (0.055 mol) of sodium bicarbonate in 20 ml. of water there was added 5.28 g. (0.018 mol) of 3-(4-fluorobenzoyl)propionic acid N-hydroxysuccinimide ester, m.p. 130°–132° C. Dioxane (300 ml.) was added and the mixture stirred for 18 hours at room temperature. The mixture was filtered and the filtrate concentrated in vacuo. The residue was partitioned between dichloromethane and dilute hydrochloric acid. The organic layer was dried over anhydrous sodium sulfate and the solvent removed in vacuo. The residue was crystallized from ether-hexane, whereby 3.0 g. of N-[3-(4-fluorobenzoyl)propionyl]-L-valine as cream colored crystals, m.p. 103°–105° C. was obtained.

To the preceding compound (0.01 mol) in acetic acid, bromine (0.01 mol) can be added. The mixture can be stirred 18 hours and the solvent removed in vacuo. The residue can be dissolved in dichloromethane and the solution washed with water and dried over magnesium sulfate. To this solution can be added 0.01 mol of potassium thioacetate, followed by stirring for 18 hours. After the addition of several drops of acetic acid, water can be added and the organic layer can be separated and dried over magnesium sulfate. The solvent can be removed in vacuo to obtain N-[3-acetylthio-3-(4-fluorobenzoyl)propionyl]-L-valine as a glass.

EXAMPLE 45

N-[3-Acetylthio-3-(4-fluorobenzoyl)propionyl]-L-alanine

Substitution of N-[3-(4-fluorobenzoyl)propionyl]-L-alanine, m.p. 122°–124° C. for N-[3-(4-fluorobenzoyl)propionyl]-L-valine in the procedure of Example 44 produces N-[3-acetylthio-3-(4-fluorobenzoyl)propionyl]-L-alanine.

EXAMPLE 46

N-[3-Acetylthio-3-(4-fluorobenzoyl)propionyl]-L-glycine

Substitution of N-[3-(4-fluorobenzoyl)propionyl]-L-glycine, m.p. 116°–119° C. for N-[3-(4-fluorobenzoyl)propionyl]-L-valine in the procedure of Example 44 produces N-[3-acetylthio-3-(4-fluorobenzoyl)propionyl]-L-glycine.

EXAMPLE 47

N-[3-Acetylthio-3-(4-fluorobenzoyl)propionyl]-L-phenylalanine

Substitution of N-[3-(4-fluorobenzoyl)propionyl]-L-phenylalanine, m.p. 153°–155° C. for N-[3-(4-fluorobenzoyl)propionyl]-L-valine in the procedure of Example 44 produces N-[3-acetylthio-3-(4-fluorobenzoyl)propionyl]-L-phenylalanine.

EXAMPLE 48

N-[3-Acetylthio-3-(3-fluorobenzoyl)propionyl]-L-phenylalanine

Substitution of N-[3-(3-fluorobenzoyl)propionyl]-L-phenylalanine for N-[3-(4-fluorobenzoyl)propionyl]-L-valine in the procedure of Example 44 produces N-[3-acetylthio-3-(3-fluorobenzoyl)propionyl]-L-phenylalanine.

EXAMPLE 49

N-[3-Acetylthio-3-(2-naphthoyl)propionyl]-L-phenylalanine

Substitution of 3-(2-naphthoyl)propionic acid for 3-(4-fluorobenzoyl)propionic acid and L-phenylalanine for L-valine in the procedure of Example 44 produces N-[3-acetylthio-3-(2-naphthoyl)propionyl]-L-phenylalanine.

EXAMPLE 50

N-[3-Acetylthio-3-(4-biphenylylcarbonyl)propionyl]-L-valine

A mixture of 50.0 g. of 3-(4-biphenylylcarbonyl)propionic acid, 23.0 g. of N-hydroxysuccinimide, 41.3 g. of N,N-dicyclohexylcarbodiimide and 400 ml. of dioxane was stirred at room temperature for 6 hours. The mixture was filtered and the filtrate concentrated in vacuo to an oil which was crystallized from chloroform-hexane to give 38 g. of crystals. Recrystallization from chloroform-ethanol gave 32 g. of the N-hydroxysuccinimide ester of 3-(4-biphenylylcarbonyl)propionic acid as cream colored crystals, m.p. 163°–164° C.

The preceding compound (6.2 g.; 0.018 mol) was added to a solution of 3.05 g. (0.026 mol) of valine and 4.62 g. (0.055 mol) of sodium bicarbonate in 150 ml. of water. Dioxane (50 ml.) was added and the mixture stirred at room temperature for 18 hours. Water (50 ml.) was added and the mixture stirred 6 hours and concentrated in vacuo to a solid. Dilute hydrochloric acid was added, followed by extraction with ethyl acetate. The ethyl acetate extract was dried oveer anhydrous sodium sulfate and the solvent removed in vacuo. The residue was crystallized from acetone-hexane to give 4.2 g. of N-[3-(4-biphenylylcarbonyl)propionyl]-L-valine as white crystals, m.p. 162°–164° C.

To the preceding compound (0.01 mol) in 25 ml. of acetic acid there can be added (0.01 mol) of bromine and anhydrous hydrogen bromide. The mixture can be stirred for 16 hours and the solvent removed in vacuo. The residue can be dissolved in acetonitrile and 0.01 mol of sodium thioacetate added. After stirring 18 hours at room temperature the solvent can be removed in vacuo to obtain N-[3-acetylthio-3-(4-biphenylylcarbonyl)propionyl]-L-valine.

EXAMPLE 51

N-[3-Acetylthio-3-(4-biphenylylcarbonyl)propionyl]-L-alanine

Substitution of N-[3-(4-biphenylylcarbonyl)propionyl]-L-alanine, m.p. 165°–166° C. for N-[3-(4-biphenylylcarbonyl)propionyl]-L-valine in the procedure of Example 50 produces N-[3-acetylthio-3-(4-biphenylylcarbonyl)propionyl]-L-alanine.

EXAMPLE 52

N-[3-Acetylthio-3-(4-biphenylylcarbonyl)propionyl]-L-glycine

Substitution of N-[3-(4-biphenylylcarbonyl)priopionyl]-L-glycine, m.p. 169°-172° C. for N-[3-(4-biphenylylcarbonyl)propionyl]-L-valine in the procedure of Example 50 produces N-[3-acetylthio-3-(4-biphenylylcarbonyl)propionyl]-L-glycine.

EXAMPLE 53

N-[3-Acetylthio-3-(4-biphenylylcarbonyl)propionyl]-L-phenylalanine

Substitution of N-[3-(4-biphenylylcarbonyl)propionyl]-L-phenylalanine, m.p. 147°-150° C. for N-[3-(4-biphenylylcarbonyl)propionyl]-L-valine in the procedure of Example 50 produces N-[3-acetylthio-3-(4-biphenylylcarbonyl)propionyl]-L-phenylalanine.

EXAMPLE 54

N-[3-Acetylthio-3-(4-biphenylylcarbonyl)propionyl]-L-leucine

Substitution of L-leucine for L-valine in the procedure of Example 50 produces N-[3-acetylthio-3-(4-biphenylylcarbonyl)propionyl]-L-leucine.

EXAMPLE 55

N-[3-Acetylthio-3-(4-biphenylylcarbonyl)propionyl]-L-sarcosine

Substitution of L-sarcosine for L-valine in the procedure of Example 50 produces N-[3-acetylthio-3-(4-biphenylylcarbonyl)propionyl]-L-sarcosine.

EXAMPLE 56

N-[3-Acetylthio-3-(4-biphenylylcarbonyl)priopionyl]-L-methionine

Substitution of L-methionine for L-valine in the procedure of Example 50 produces N-[3-acetylthio-3-(4-biphenylylcarbonyl)propionyl]-L-methionine.

EXAMPLE 57

N-[3-Acetylthio-3-(4-biphenylylcarbonyl)propionyl]-L-glutamine

Substitution of L-glutamine for L-valine in the procedure of Example 50 produces N-[3-acetylthio-3-(4-biphenylylcarbonyl)propionyl]-L-glutamine.

EXAMPLE 58

N-[3-Acetylthio-3-(3,4,5-trimethoxybenzoyl)propionyl]-L-phenylalanine

Substitution of 3-(3,4,5-trimethoxybenzoyl)propionic acid for 3-(4-bromobenzoyl)propionic acid and L-phenylalanine for L-valine in the procedure of Example 1 produces N-[3-acetylthio-3-(3,4,5-trimethoxybenzoyl)propionyl]-L-phenylalanine.

EXAMPLE 59

N-[3-Acetylthio-3-(4-bromobenzoyl)propionyl]-L-valine, methyl ester

Substitution of L-valine methyl ester in the procedure of Example 1 produces N-[3-acetylthio-3-(4-bromobenzoyl)propionyl]-L-valine, methyl ester.

EXAMPLE 60

N-[3-Acetylthio-3-(4-methoxybenzoyl)propionyl]-L-phenylalanine, ethyl ester

Substitution of L-phenylalanine, ethyl ester, for L-valine in the procedure of Example 5 produces N-[3-acetylthio-3-(4-methoxybenzoyl)propionyl]-L-phenylalanine, ethyl ester.

EXAMPLE 61

N-[3-Acetylthio-3-(3-fluoro-4-methoxybenzoyl)propionyl]-L-alanine, methyl ester

Substitution of L-alanine, methyl ester for L-valine in the procedure of Example 21 produces N-[3-acetylthio-3-(3-fluoro-4-methoxybenzoyl)propionyl]-L-alanine, methyl ester.

EXAMPLE 62

N-[3-Acetylthio-3-(benzoyl)propionyl]-L-sarcosine, ethyl ester

Substitution of L-sarcosine, ethyl ester for L-valine in the procedure of Example 40 produces N-[3-acetylthio-3-(benzoyl)propionyl]-L-sarcosine, ethyl ester.

EXAMPLE 63

N-[3-Acetylthio-3-(benzoyl)propionyl]-L-glycine, ethyl ester

Substitution of L-glycine, ethyl ester in the procedure of Example 40 produces N-[3-acetylthio-3-(benzoyl)propionyl]-L-glycine, ethyl ester.

EXAMPLE 64

N-[3-Acetylthio-3-(benzoyl)-2-methylpropionyl]-L-valine

Substitution of 3-(benzoyl)-2-methylpropionic acid for 3-(benzoyl)propionic acid in the procedure of Example 40 produces N-[3-acetylthio-3-(benzoyl)-2-methylpropionyl]-L-valine.

EXAMPLE 65

N-[3-Acetylthio-3-(benzoyl)-2-methylpropionyl]-L-phenylalanine

Substitution of 3-(benzoyl)-2-methylpropionic acid for 3-(benzoyl)propionic acid and L-phenylalanine for L-valine in the procedure of Example 40 produces N-[3-acetylthio-3-(benzoyl)-2-methylpropionyl]-L-phenylalanine.

EXAMPLE 66

N-[2-Acetylthio-3-(benzoyl)propionyl]-L-valine

To a solution of 26.4 g. of benzoylacrylic acid and 17.25 g. of N-hydroxysuccinimide in 165 ml. of dioxane there was added a solution of 30.9 g. of N,N-dicyclohexylcarbodiimide in 120 ml. of dioxane. The mixture was stirred at room temperature for 18 hours and filtered. The filtrate was concentrated to dryness in vacuo. The residual oil was triturated with hexane, producing a waxy solid. The solid was crystallized from dichloromethane-hexane to give 18.2 g. of the N-hydroxysuccinimide ester of benzoylacrylic acid as yellow crystals.

The preceding compound (0.01 mol) can be added to 0.01 mol of L-valine and 0.02 mol of sodium bicarbonate in dioxane-water (1:2). After stirring 18 hours, the mixture can be filtered and the filtrate acidified with concentrated hydrochloric acid. The mixture can be extracted with dichloromethane to obtain N-(3-benzoylacryloyl)-L-valine.

The preceding compound can be dissolved in dichloromethane and 0.02 mol of thioacetic acid can be added. After stirring for 8 hours, the solvent can be removed to obtain N-[2-acetylthio-3-(benzoyl)propionyl]-L-valine.

EXAMPLE 67

N-[2-Acetylthio-3-(benzoyl)propionyl]-L-alanine

Substitution of L-alanine for L-valine in the procedure of Example 66 produces N-[2-acetylthio-3-(benzoyl)propionyl)]-L-alanine.

EXAMPLE 68

N-[2-Acetylthio-3-(benzoyl)propionyl]-L-phenylalanine

Substitution of L-phenylalanine for L-valine in the procedure of Example 66 produces N-[2-acetylthio-3-(benzoyl)propionyl]-L-phenylalanine.

EXAMPLE 69

N-[2-Acetylthio-3-(benzoyl)propionyl]-L-glycine

Substitution of L-glycine for L-valine in the procedure of Example 66 produces N-[2-acetylthio-3-(benzoyl)propionyl]-L-glycine.

EXAMPLE 70

N-[2-Acetylthio-3-(benzoyl)propionyl]-L-glutamine

Substitution of L-glutamine for L-valine in the procedure of Example 66 produces N-[2-acetylthio-3-(benzoyl)propionyl]-L-glutamine.

EXAMPLE 71

N-[2-Acetylthio-3-(benzoyl)propionyl]-S-methyl-L-cysteine

Substitution of S-methyl-L-cysteine for L-valine in the procedure of Example 66 produces N-[2-acetylthio-3-(benzoyl)propionyl]-S-methyl-L-cysteine.

EXAMPLE 72

N-[2-Acetylthio-3-(benzoyl)propionyl]-L-sarcosine

Substitution of L-sarcosine for L-valine in the procedure of Example 66 produces N-[2-acetylthio-3-(benzoyl)propionyl]-L-sarcosine.

EXAMPLE 73

N-(3-Benzoyl-2-methylpropionyl)-L-cysteine

To a solution of 10.5 g. (0.06 mol) of L-cysteine hydrochloride monohydrate, 18.0 g. (0.18 mol) of potassium bicarbonate in 60 ml. of water there was added 17.34 g. (0.06 mol) of 3-benzoyl-2-methylpropionic acid, N-hydroxysuccinimide ester, in 60 ml. of acetonitrile. The mixture was stirred two days under argon, then filtered rapidly and the filtrate concentrated in vacuo. To the residue was added ice, water and ethyl acetate. The mixture was acidified with dilute hydrochloric acid. The organic layer was separated, dried over anhydrous sodium sulfate and concentrated in vacuo. The residue was partitioned between saturated sodium carbonate and ethyl acetate. The aqueous layer was added dropwise to a mixture of dilute hydrochloric acid and ice. The mixture was extracted with ethyl acetate and the organic layer separated, dried over anhydrous sodium sulfate and concentrated in vacuo, giving 15.5 g. of a yellow gum. The gum was purified by chromatography on silica gel using a Waters Prep 500 apparatus with a solvent system consisting of ethyl acetate-hexane-acetic acid. Washing the column with ethyl acetate-acetic acid (4:1) gave an oil which was crystallized from ethyl acetate-hexane giving N-(3-benzoyl-2-methylpropionyl)-L-cysteine as white crystals, m.p. 78°–105° C. (mixture of diastereomers).

EXAMPLE 74

N-[3-Acetylthio-3-(benzoyl)-2-methylpropionyl]-L-alanine

To a solution of 4.64 g. (0.052 mol) of L-alanine and 9.24 g. (0.11 mol) of sodium bicarbonate in 100 ml. of water there was added 10.4 g. (0.036 mol) of 3-benzoyl-2-methylpropionic acid, N-hydroxysuccinimide ester. Dioxane (50 ml.) and tetrahydrofuran (50 ml.) were added and the mixture stirred at room temperature for 2 days. The mixture was concentrated in vacuo and the residue partitioned between dichloromethane and dilute hydrochloric acid. The organic layer was separated and dried over anhydrous sodium sulfate. The solvent was removed in vacuo to give 10.0 g. of a yellow gum. The gum was chromatographed on silica gel with ethyl acetate-hexane-acetic acid (75:25:1) as solvent to give 4.4 g. of a solid intermediate compound. The solid was reprecipitated from hexane-ether to give a white solid. To the preceding compound (0.01 mol) in 25 ml. of acetic acid there can be added (0.01 mol) of bromine. After stirring 18 hours, the solvent can be removed and the residue reacted with 0.01 mol of potassium thioacetate in acetonitrile for 24 hours. The solvent can be removed in vacuo to obtain N-[3-acetylthio-3-(benzoyl)-2-methylpropionyl]-L-alanine as a glass.

EXAMPLE 75

N-Methyl-N-[3-acetylthio-3-(benzoyl)-2-methylpropionyl]-L-phenylalanine

Substitution of N-methylphenyl-L-alanine for L-alanine in the procedure of Example 74 produces N-methyl-N-[[3-acetylthio-3-(benzoyl)-2-methyl]propionyl]-L-phenylalanine as a glass.

EXAMPLE 76

N-[3-Acetylthio-3-(benzoyl)-2-methylpropionyl]-O-benzyl-L-serine

Substitution of O-benzyl-L-serine for L-alanine in the procedure of Example 74 produces N-[[3-acetylthio-3-(benzoyl)-2-methyl]propionyl]-O-benzyl-L-serine as a glass.

EXAMPLE 77

[S-(R*,S*)]-N-[3-Acetylthio-3-(benzoyl)-2-methylpropionyl]-L-alanine and
[S-(R*,R*)]-N-[3-acetylthio-3-(benzoyl)-2-methylpropionyl]-L-alanine To a solution of 36.5 g. (0.41 mol) of L-alanine and 68.88 g. (0.82 mol) of sodium bicarbonate in one liter of water there was added 83.0 g. (0.287 mol) of N-hydroxysuccinimide ester of L-alanine and 200 ml. of dioxane. The mixture was stirred for 5 days. The mixture was filtered and the solvent removed under reduced pressure. To the residue there was added water and dilute hydrochloric acid. The mixture was extracted with dichloromethane. The extract was dried over anhydrous sodium sulfate and the solvent removed in vacuo.

A 2.4 g. amount of the residue was purified by chromatography on a Waters Prep 500 chromatographic apparatus with a solvent system of hexane-ethyl acetate (7:3) containing 0.25% formic acid. The main fraction was crystallized from dichloromethane-hexane and gave 1.1 g. of crystals of [R]-N-[(3-benzoyl-2-methylpropionyl)]-L-alanine, m.p. 117°-119° C.; $[\alpha]_D^{23}$-5°±1 (c, 0.876, $CH_3OH$).

The preceding compound can be brominated with bromine in acetic acid and the resulting bromo derivative can be reacted with potassium thioacetate as described in the procedure of Example 1 to obtain [S-(R*,S*)]-N-[3-acetylthio-3-(benzoyl)-2-methylpropionyl]-L-alanine and [S-(R*,R*)]-N-[3-acetylthio-3-(benzoyl)-2-methylpropionyl]-L-alanine.

Having thus described the invention, what is claimed is:

1. Compounds represented by the formula $$\underset{ARYL}{}-\overset{O}{\underset{\|}{C}}-Z-\overset{O}{\underset{\|}{C}}-\overset{R_1}{\underset{|}{N}}-\overset{R_2}{\underset{|}{C}}HCO_2R_3$$

wherein Z is a divalent moiety selected from the class consisting essentially of $$-\overset{R_5}{\underset{|}{C}H}-\overset{}{\underset{|}{C}H}- \text{ and } -\overset{R_5}{\underset{|}{C}H}-\overset{}{\underset{|}{C}H}-;$$
$$\qquad\; SR_4 \qquad\qquad\qquad SR_4$$

$R_1$ is selected from the class consisting essentially of hydrogen and lower alkyl having from 1 to 4 carbon atoms but excluding tertiary butyl; $R_2$ is selected from the class consisting essentially of hydrogen, lower alkyl having from 1 to 4 carbon atoms but excluding tertiary butyl; hydroxy—$R_8$—, lower alkyl—$R_8$—, mercapto—$R_8$—, cyclohexyl, cyclopentyl, phenyl, phenyl—$R_8$—, carboxy—$R_8$—, amino—$R_8$— and carbamoyl—$R_8$—, wherein $R_8$— is a divalent straight chain parafinic moiety having 1 to 6 carbon atoms; $R_3$ is selected from the class consisting essentially of hydrogen and lower alkyl having from 1 to 4 carbon atoms; $R_4$ is selected from the class consisting essentially of hydrogen, lower alkanoyl, benzoyl and phenyl-substituted-lower alkanoyl; $R_5$ is selected from the class consisting essentially of hydrogen and a lower alkyl having from 1 to 4 carbon atoms but excluding tertiary butyl; ARYL is selected from the class consisting essentially of 1-naphthyl, 2-naphthyl, 4-chloro-1-naphthyl, 4-methoxy-1-naphthyl, 5,6,7,8-tetrahydro-1-naphthyl, 5,6,7,8-tetrahydro-2-naphthyl, 4-biphenylyl, 5-indanyl, 4-indanyl, phenyl, and substituted phenyl moieties having the formula $$R_6 \diagdown \hspace{-10pt}\bigcirc \hspace{-10pt}\diagup (R_7)_m$$

wherein $R_6$ is selected from the class consisting essentially of fluoro, chloro, bromo, trifluoromethyl, cyano, phenoxy, halophenoxy, phenylthio, halophenylthio, lower alkyl having from 1 to 4 carbon atoms, and lower alkoxy having from 1 to 4 carbon atoms, and $R_7$ is selected from the group consisting of chloro, fluoro, bromo, lower alkyl having from 1 to 4 carbon atoms and lower alkoxy having from 1 to 4 carbon atoms; and where m is an integer of zero, one or two; including individual optically active isomers; racemic mixtures thereof; non-toxic pharmacologically-acceptable salts of the foregoing; and mixtures of the foregoing.

2. Compounds of claim 1 wherein Z is $$-\overset{R_5}{\underset{|}{C}H}-\overset{}{\underset{|}{C}H}-.$$
$$\;\; SR_4$$

3. Compounds of claim 1 wherein $R_3$ is hydrogen.

4. Compounds of claim 1 wherein $R_4$ is selected from the class consisting of acetyl and propionyl.

5. Compounds of claim 1 wherein ARYL is selected from the class consisting essentially of 2-naphthyl, 4-biphenyl, 5-indanyl, phenyl and substituted phenyl wherein $R_6$ is selected from the class consisting essentially of fluoro, chloro, bromo phenoxy or halophenoxy, and the integer m is zero.

6. Compounds of claim 1 wherein $R_8$ has 1 to 3 carbon atoms.

7. Compounds of claim 1 wherein $R_4$ is acetyl, ARYL is phenyl or a substituted phenyl, and $R_3$ is hydrogen, non-toxic pharmacologically-acceptable cationic salts thereof, and mixtures of said compounds.

8. Compounds according to claim 1, N-[3-acetylthio-3-(4-bromobenzoyl)propionyl]-L-valine.

9. Compounds according to claim 1, N-[3-acetylthio-3-(3-fluoro-4-methoxybenzoyl)propionyl]-3-phenyl-L-alanine.

10. Compounds according to claim 1, N-[3-acetylthio-3-(benzoyl)propionyl]-L-alanine.

11. Compounds according to claim 1, N-[3-acetylthio-3-(benzoyl)-2-methylpropionyl]-L-alanine.

12. The isomer of the compounds of claim 11 which is [S-[R*,S*]-N-[3-acetylthio-3-(benzoyl)-2-methylpropionyl]-L-alanine.

13. Compounds according to claim 1, N-[3-acetylthio-3-(benzoyl)-2-methylpriopionyl]-L-sarcosine.

14. Compounds according to claim 1, N-[3-acetylthio-3-(4-chlorobenzoyl)-2-methylpropionyl]-L-phenylalanine.

15. The compound according to claim 1, N-[3-acetylthio-3-[4-(4-chlorophenoxy)benzoyl]-2-methylpropionyl]-L-phenylalanine.

16. The compound according to claim 1, N-[3-acetylthio-3-(2-naptoyl)-2-methylpropionyl]-L-phenylalanine.

17. The compound according to claim 1, N-[3-acetylthio-3-(1-naphthoyl)-2-methylpropionyl]-L-sarcosine.

18. The compound according to claim 1, N-[3-acetylthio-3-(3,4,5-trimethoxybenzoyl)-2-methylpropionyl]-S-methyl-L-cysteine.

19. The compound according to claim 1, N-[3-acetylthio-3-(benzoyl)-2-methylpropionyl]-O-benzyl-L-serine.

20. The compound according to claim 1, N-[2-acetylthio-3-(benzoyl)propionyl]-L-valine.

21. The compound according to claim 1, N-[2-acetylthio-3-(4-tert-butylbenzoyl)propionyl]-L-phenylalanine.

* * * * *